(12) United States Patent
Gordon et al.

(10) Patent No.: US 10,098,871 B2
(45) Date of Patent: Oct. 16, 2018

(54) COMBINATION THERAPIES FOR TREATMENT OF LAMINOPATHIES, CELLULAR AGING, AND ATHEROSCLEROSIS

(71) Applicants: Leslie B. Gordon, Foxboro, MA (US); Mark W. Kieran, Newton, MA (US); Monica E. Kleinman, Sharon, MA (US)

(72) Inventors: Leslie B. Gordon, Foxboro, MA (US); Mark W. Kieran, Newton, MA (US); Monica E. Kleinman, Sharon, MA (US)

( * ) Notice: Subject to any disclaimer, the term of this patent is extended or adjusted under 35 U.S.C. 154(b) by 0 days.

(21) Appl. No.: 15/201,525

(22) Filed: Jul. 4, 2016

(65) Prior Publication Data

US 2016/0310473 A1    Oct. 27, 2016

Related U.S. Application Data

(63) Continuation-in-part of application No. 14/209,197, filed on Mar. 13, 2014, now Pat. No. 9,381,203.

(60) Provisional application No. 61/815,497, filed on Apr. 24, 2013, provisional application No. 61/786,565, filed on Mar. 15, 2013.

(51) Int. Cl.
| | |
|---|---|
| *A61K 31/21* | (2006.01) |
| *A61K 31/44* | (2006.01) |
| *A61K 31/675* | (2006.01) |
| *A61K 31/436* | (2006.01) |
| *A61K 31/4545* | (2006.01) |
| *A61K 9/00* | (2006.01) |
| *A61K 9/20* | (2006.01) |
| *A61K 45/06* | (2006.01) |
| *A61K 31/22* | (2006.01) |
| *A61K 31/55* | (2006.01) |
| *A61K 31/663* | (2006.01) |

(52) U.S. Cl.
CPC .......... *A61K 31/436* (2013.01); *A61K 9/0053* (2013.01); *A61K 9/20* (2013.01); *A61K 31/22* (2013.01); *A61K 31/4545* (2013.01); *A61K 31/675* (2013.01); *A61K 45/06* (2013.01); *A61K 31/55* (2013.01); *A61K 31/663* (2013.01)

(58) Field of Classification Search
CPC ........................... A61K 31/436; A61K 31/663
USPC ........................................... 514/514, 290, 94
See application file for complete search history.

(56) References Cited

U.S. PATENT DOCUMENTS

| | | | | |
|---|---|---|---|---|
| 5,665,772 A | * | 9/1997 | Cottens | C07D 498/18 514/514 |
| 7,838,531 B2 | * | 11/2010 | Gordon | A61K 31/4545 424/9.2 |
| 8,828,356 B2 | * | 9/2014 | Gordon | A61K 31/4545 424/9.2 |
| 9,381,203 B2 | * | 7/2016 | Gordon | A61K 31/675 |

OTHER PUBLICATIONS

Capell et al., "Inhibiting farnesylation of progerin prevents the characteristic nuclear blebbing of Hutchinson-Gilford progeria syndrome", Proceedings of the National Academy of Sciences of the USA, vol. 102, No. 36, pp. 12879-12884 (2005).*
Varela et al., "Combined treatment with statins and aminobisphosphonates extends longevity in a mouse model of human premature aging", Nature Medicine, vol. 14, No. 7, pp. 767-772 (2008).
Mendelsohn et al., "Rapamycin as an Antiaging Therapeutic?: Targeting Mammalian Target of Rapamycin to Treat Hutchinson-Gilford Progeria and Neurodegenerative Diseases", Rejuvenation Research, vol. 14, No. 4, pp. 437-441 (2011).

* cited by examiner

*Primary Examiner* — Kevin E Weddington
(74) *Attorney, Agent, or Firm* — JMB Davis Ben-David

(57) ABSTRACT

Provided herein are combination therapies for the treatment of progeroid diseases and conditions, cellular aging, bone diseases, and cardiovascular diseases. The provided combination therapies target the aberrant farnesylation of the mutant lamin A protein progerin and increase progerin clearance.

6 Claims, 5 Drawing Sheets

Mean Survival (Years) = Area Under Kaplan-Meier Curve

| Grouping | Untreated Patients | Treated Patients | Difference |
|---|---|---|---|
| All Patients | 14.2 | 18.8 | 4.6 |
| Patients Born on or after 1991 | 13.1 | 18.8 | 5.7 |
| Starting at age 3 years | 14.3 | 18.8 | 4.5 |
| Matched Sample | 15.0 | 18.8 | 3.8 |
| Matched Sample – Patients Born on or after 1991 | 13.8 | 18.6 | 4.8 |

Figure 5

COMBINATION THERAPIES FOR TREATMENT OF LAMINOPATHIES, CELLULAR AGING, AND ATHEROSCLEROSIS

CROSS REFERENCE TO RELATED APPLICATIONS

The is a Continuation-in-Part of co-pending U.S. patent application Ser. No. 14/209,197, filed Mar. 13, 2014, which claims the benefit to U.S. Provisional Patent Application No. 61/815,497, filed Apr. 24, 2013; and U.S. Provisional Patent Application No. 61/786,565, filed Mar. 15, 2013. The contents of the foregoing patent applications are incorporated by reference herein in their entirety.

ACKNOWLEDGMENT OF GOVERNMENT SUPPORT

This invention was made in part with government support under grant number 1RC2HL101631-1 awarded by the National Institutes of Health, National Heart, Lung, and Blood Institute. The government may have certain rights in one or more claims that may issue from this patent application.

FIELD

Provided herein are combination therapies for the treatment of progeroid diseases and conditions, cellular aging, and cardiovascular and bone diseases.

BACKGROUND

Hutchinson-Gilford Progeria Syndrome (HGPS) is a rare genetic disease that becomes apparent usually in the first year of life, and causes a phenotype resembling many aspects of aging. Affected children have a remarkably similar appearance, despite differing ethnic backgrounds, and die of premature atherosclerosis at an average age of 13 years. Progeria is a disease in which some, but not all, of its clinical manifestations represent a model of accelerated aging (reviewed in Sweeney & Weiss, *Gerontology* 38:139-52, 1992). Although they are born looking healthy, children with Progeria begin to display many characteristics of accelerated aging at around 18-24 months of age. Clinical features common to progeria and normal aging include alopecia (although the pattern of hair loss differs), sclerodermatosis, atherosclerosis, lipofuscin deposition, nail dystrophy, hypermelanosis, decreased adipose tissue, and osteoporosis.

With the identification of the gene responsible for HGPS, it was determined that HGPS is a type of laminopathy, a group of diseases associated with an underlying defect in the lamin A/C gene (LMNA) (Eriksson et al., *Nature* 423:293-298, 2003; and U.S. Pat. No. 7,297,492). LMNA codes for the lamin A and lamin C isoforms, which differ due to alternate splicing. The lamins are a component of the nuclear lamina, a fibrous matrix located at the interior of the nuclear membrane, responsible for nuclear integrity and organization (Gruenbaum et al., *J Struct Biol* 129:313-23, 2000; Gruenbaum et al., *Nat. Rev. Mol. Cell Biol.* 6:21-31, 2005).

Nearly all HGPS patients have the same silent mutation (G608G) creating an abnormal splice donor site in exon 11 of the LMNA gene (Eriksson et al., *Nature* 423:293-298, 2003), which causes a 150 base pair mRNA deletion in the lamin A transcript. The result of the mis-splicing is a protein missing 50 amino acids near the C-terminus (henceforth called "preprogerin" prior to posttranslational processing and "progerin" after post-translational processing). The deleted region includes the protein cleavage site that normally removes the C-terminal 15 amino acids, including a cysteine, which is farnesylated during posttranslational processing. The absence of this proteolytic cleavage site results in a protein which remains farnesylated. Persistently-farnesylated progerin is aberrantly anchored at the inner nuclear membrane and is at least partly responsible for the HGPS cellular phenotypes of nuclear abnormalities and premature apoptosis. Accordingly, it was proposed that inhibition of farnesyltransferase might provide treatment for HGPS (see U.S. Pat. No. 7,297,492). In addition, any abnormality in the lamin A processing pathway can lead to a laminopathy which might benefit from farnesylation or mTOR inhibition.

Promising pre-clinical studies demonstrated the use of farnesyltransferase inhibitors (FTIs) to inhibit and even reverse characteristic HGPS phenotypes of progerin accumulation and nuclear structural abnormalities (see for examples, U.S. Pat. No. 7,838,531 and references cited therein). Similarly, clinical trials of an FTI in HGPS patients demonstrated improvement in several disease aspects, including weight gain, improvements in skeletal rigidity, and improvements in cardiovascular function (Gordon et al., *PNAS*, 109:16666/16671, 2012).

The clinical trial of FTI treatment in HGPS patients demonstrated some therapeutic benefits of FTI treatment for children with Progeria, but the therapeutic benefit is not complete. Additionally, the increased presence of progerin has been correlated with cardiovascular disease and senescence in non-HGPS subjects (Olive et al., *Arterioscler. Thromb. Vasc. Biol.*, 30:2301-2309, 2010; and McClintock et al., *PLoS One*, 2:e1269, 2007). Accordingly, a need continues to exist to develop improved treatments for abnormal lamin A-related conditions including HGPS and related laminopathies, abnormal lamin A-related cardiovascular conditions, and other age-related disease.

SUMMARY

Provided herein are methods of treating a subject having or susceptible to a progeroid disease or condition, a cellular aging-related condition, a bone disease, or a cardiovascular disease or condition, all of which result from expression of progerin, a mutant lamin A protein, or an abnormal lamin A protein such as overabundance of prelamin A. The described methods involve administering to a subject in need of such treatment, a therapeutically effective dose of at least two active ingredients including: (a) a farnesyltransferase inhibitor (FTI), such as lonafarnib; and (b) an mTOR inhibitor, such as everolimus.

The foregoing and other objects, features, and advantages will become more apparent from the following detailed description, which proceeds with reference to the accompanying figures.

BRIEF DESCRIPTION OF THE DRAWINGS

FIG. 5 is a summary chart showing the results of Kaplan-Meier survival analyses comparing HGPS patients who were with treated with lonafarnib (including patients treated with lonafarnib; pravastatin; zoledronic acid), with patients were not treated with any farnesyltransferase inhibitor. Mean survival is shown for: all subjects, patients born on or after 1991, patients starting at three years of age, a matched sample of the available data, and a matched sample of the subset of patients born on or after 1991.

DETAILED DESCRIPTION

I. Abbreviations

Figure 1:
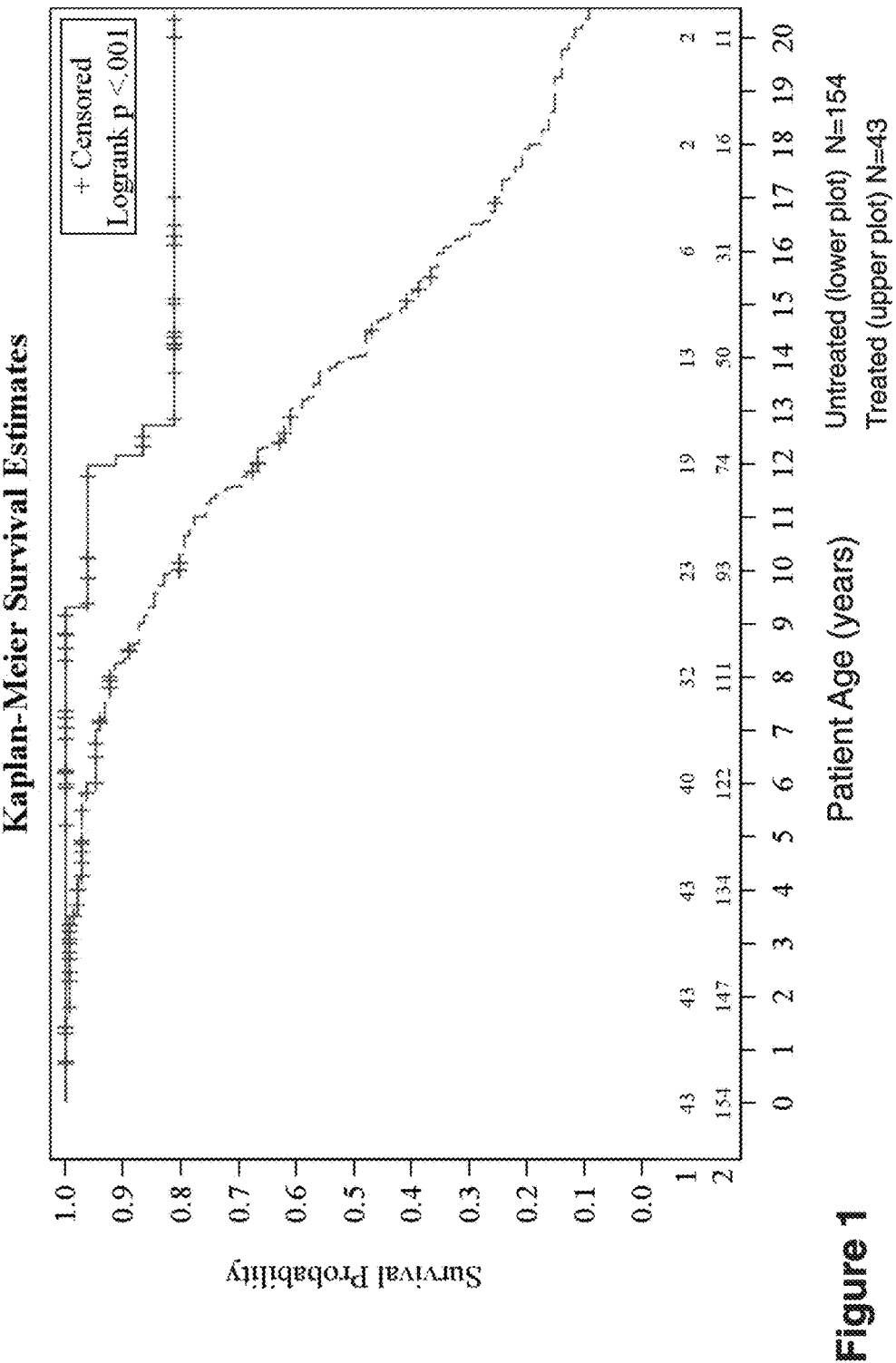
FIG. 1 shows the results of a Kaplan-Meier survival analysis comparing HGPS patients who were with treated with lonafarnib (including patients treated with lonafarnib; pravastatin; zoledronic acid), with patients were not treated with any farnesyltransferase inhibitor. Untreated subjects are shown in the lower plot. Treated subjects are shown in the upper plot.

FPP: farnesyl pyrophosphate
FTase: farnesyltransferase
FTI: farnesyltransferase inhibitor
GGTase I: geranylgeranyltransferase
GGTI: geranylgeranyltransferase inhibitor
HGPS: Hutchinson-Gilford Progeria Syndrome
LMNA: gene encoding lamin A and lamin C
mTOR: mammalian target of rapamycin

II. Terms

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below. The term "comprises" means "includes." The abbreviation, "e.g." is derived from the Latin exempli gratia, and is used herein to indicate a non-limiting example. Thus, the abbreviation "e.g." is synonymous with the term "for example."

In addition, all the materials, methods, and examples are illustrative and not intended to be limiting.

III. Overview of Several Embodiments

Provided herein are methods of treating a subject having or susceptible to a progeroid disease or condition, a cellular aging-related condition, a bone disease or a cardiovascular disease or condition, all of which are resultant from expression of progerin, a mutant lamin A protein or an abnormal lamin A protein such as overabundance of prelamin A. The described methods involve administering to a subject in need of such treatment, a therapeutically effective dose of at least two active ingredients including: (a) a farnesyltransferase inhibitor (FTI), such as lonafarnib; and (b) an mTOR inhibitor, such as everolimus.

In particular examples, the progeroid disease is Hutchinson-Gilford Progeria Syndrome. In other examples, the cellular aging related-condition is aberrant cellular senescence. In still other examples, the cardiovascular disease is atherosclerosis or arteriosclerosis.

In a particular example, the lonafarnib is administered at a dosage between 115 mg/m$^2$ and 150 mg/m$^2$.

In some examples, the at least two pharmaceutical compositions are administered simultaneously. In other examples, the at least two pharmaceutical compositions are not administered simultaneously, such as, but not limited to different times of day or different days of the week, or different weeks of the month.

IV. Combination Therapies for Treatment of Progerin-Related Conditions

Described herein are methods of treating a progerin-related or lamin A-related disease or condition using combinations of therapeutic agents. One embodiment of the treatment combinations described herein provides at least two pharmaceutical agents, including a FTI, and an inhibitor of mTOR signaling.

The combination therapies described herein involve multiple components, such as at least two, at least three, or at least four or more therapeutic components. It is also understood that a combination therapy may include a non-pharmaceutical component (e.g. physical therapy, radiation therapy, surgical interventions, and the like).

The methods described herein are directed to treating a progerin-related or lamin A-related disease or condition in a subject having or susceptible to having such a disease.

The therapies described herein are directed at progerin-related or lamin A-related diseases and conditions (e.g. diseases related to aberrant accumulation of prelamin A and the like), including HGPS or another progeroid disease (as described in U.S. Pat. No. 7,297,492, the contents of which are incorporated by reference in their entirety), cellular aging-related conditions associated with cellular senescence and progerin-related cellular defects (as described in U.S. Pat. No. 7,838,531, the contents of which are incorporated by reference in their entirety), bone diseases, and cardiovascular diseases or conditions (such as, but not limited to, atherosclerosis and arteriosclerosis).

The described methods include administering combinations at least two active ingredients (FTI, and mTOR inhibitor), to the subject. Each pharmaceutical agent can be separately formulated in a pharmaceutically compatible carrier and in an amount effective to inhibit the development or progression of a disease. Although the combination treatments can be used prophylactically in any patient in a demographic group at significant risk for such progerin-related or lamin A-related diseases, subjects can also be selected using more specific criteria, such as a definitive diagnosis of the disease/condition or identification of one or more factors that increase the likelihood of developing such disease (e.g., detectable LMNA mutation, cellular progerin concentration, and the like).

Farnesyltransferase Inhibitors

One component of the combination treatments described herein is a farnesyltransferase inhibitor. Farnesyltransferase inhibitors (FTIs) are a class of compounds which inhibit the ability of farnesyltransferase to transfer a farnesyl group from farnesyl pyrophosphate to a given target protein. FTIs can be used to inhibit the addition of farnesyl to progerin, thereby preventing the aberrant association of progerin or prelamin A with the inner nuclear envelope.

FTIs were developed originally as inhibitors of Ras biological activity (Reuter et al., *Blood* 96(5):1655-1669, 2000). FTIs generally can be divided into three groups: (1) tetrapeptides having or mimicking the CAAX motif (Brown et al., *Proc. Natl. Acad. Sci. U.S.A.* 89:8313-8316, 1992; Reiss et al., *Proc. Natl. Acad. Sci. U.S.A.* 88:732-736, 1991; Goldstein et al., *J. Biol. Chem.* 266:15575-15578, 1991); (2) analogs of farnesyl pyrophosphate (FPP) (Gibbs et al., *J. Biol. Chem* 268:7617-7620, 1993); and (3) inhibitors with structures not resembling either tetrapeptides or FPP (Liu et al., *J. Antibiot.* 45:454-457, 1992; Miura et al., *FEBS Lett.* 318:88-90, 1993; Omura et al., *J. Antibiot.* 46:222-228, 1993; Van Der Pyl et al. *J. Antibiot.* 45:1802-1805, 1992). The latter category of inhibitors generally has lower activity compared to the first two categories. By way of example, the FTI lonafarnib (also known as SCH66336 and Sarasar®) is a non-peptidomimetic FTI; FTI-277 is a peptidomimetic. Another non-limiting example of a FTI for use in the methods described herein include R115777 (tipifarnib, Zarnestra®). The development and chemistry of FTIs are well documented and known to those of ordinary skill. By way of example, the following publications review FTIs in the context of cancer treatment: Cox & Der, *Biochim Biophys Acta* 1333:F51-F71, 1997; Gelb et al., *Curr Opin Chem Biol* 2:40-48, 1998; Rowinsky et al., *J. Clin Oncol.* 17; 3631-3652, 1999; Oliff, *Biochim Biophys Acta* 1423:C19-C30, 1999; Sebti & Hamilton, *Expert Opin Investig Drugs* 9:2767-2782, 2000; and Gibbs et al., *Curr Med Chem* 8:1437-1465, 2001.

It has previously been shown that FTIs can be used to reverse and/or prevent cellular effects caused by accumulation of progerin or other forms of farnesylated lamin A (see U.S. Pat. No. 7,838,531). It is believed that all categories of FTIs can be used in methods and compositions provided herein; the selection of a specific FTI is within the skill of the ordinary practitioner based on testing methods provided herein. In some embodiments, it is beneficial to select an inhibitor compound that is more selective for farnesyltransferase, compared to geranylgeranyltransferase I. In other embodiments, it may be beneficial to select an inhibitor compound that is dually selective, in that it inhibits both FTase and GGTase I. Considerations for determining selectivity criteria for FTIs include (but are not limited to) the possibility of lower toxicity with FTase-specific FTIs versus dual specificity FTIs, although both efficacy and toxicity may differ according to the particular compound and the particular patient. As will be recognized by an ordinarily skilled practitioner, other considerations, for instance pharmacological and medical considerations, may also apply.

In particular examples, the FTI, such as lonafarnib is administered at a dosage range between 115 mg/m$^2$ to 150 mg/m$^2$/day, such as about 115 mg/m$^2$, 120 mg/m$^2$, 125 mg/m$^2$, 130 mg/m$^2$, 135 mg/m$^2$, 140 mg/m$^2$, 145 mg/m$^2$, 150 mg/m$^2$. One of skill will appreciate that other dosage ranges typical for FTIs are encompassed by this disclosure.

mTOR Inhibitors

The mammalian target of rapamycin (mTOR) is a serine/threonine protein kinase associated with myriad cellular processes including growth, proliferation, and metabolism (for review, see Baldo et al., *Current Cancer Drug Targets*, 8:647-665, 2008). mTOR inhibitors are currently being investigated for multiple clinical uses, including anti-proliferative and anti-angiogenic effects (Id.). Recently, it was observed the mTOR inhibitor rapamycin inhibited several hallmark phenotypes of HGPS fibroblasts and enhanced progerin degradation and clearance in both HGPS and normal cells (Cao et al., *Science Trans. Med.*, 3:89ra58, 2011).

Non-limiting examples of mTOR inhibitors for use in the described combination treatments include: rapamycin (or sirolimus), everolimus, temsirolimus, deforolimus, ridaforolimus, nab-rapamycin, salirasib or any derivative of any of the above which retains mTOR inhibition function. mTOR inhibitor dosage regimens vary depending on the particular pharmaceutical compound. In a particular embodiment, rapamycin is administered to an adult in a daily dosage within the range including, but not limited to, 1 mg-5 mg/kg, such as 1 mg, 2 mg, 3 mg, 4 mg, and 5 mg. In another embodiment, everolimus is administered to an adult in a daily dosage within the range including, but not limited to 0.25 mg-1.0 g, such as 0.25 mg, 0.50 mg, 0.75 mg, and 1.0 g/kg. One of skill will appreciate that adult dosages may not be suitable for children, or adults and children with a progeroid disease or condition. mTOR inhibitor (such as everolimus) dosages can therefore be accordingly adjusted to be suitable for the particular patient to be treated. In a particular embodiment, everolimus is administered at a dosage between 1-5 mg/m$^2$/day, such as 1, 2, 3, 4, or 5 mg/m$^2$/day In particular examples, the mTOR inhibitor component of the described combination therapies can be administered simultaneously with the other components described herein. In other examples, the administered mTOR inhibitor is given separately from the other components. In some examples, the mTOR inhibitor is administered in a single dose. In other examples the mTOR inhibitor is administered in multiple dosages.

Pharmaceutical Compositions and Modes of Administration

It is contemplated that the pharmaceutical agents for use in the described combination treatments can be supplied in any pharmaceutically acceptable composition.

In particular embodiments, a FTI and an mTOR inhibitor are combined in a single pharmaceutical formulation having a therapeutically effective dose of each therapeutic agent, as described herein. In other embodiments, the FTI and mTOR inhibitor are formulated as separate pharmaceutical compositions which can be administered concurrently or separately.

Among the pharmaceutical compositions specifically contemplated in the present disclosure are pharmaceutically acceptable acid or base addition salts of FTIs and mTOR inhibitors. The phrase "pharmaceutically acceptable acid or base addition salts" includes therapeutically active non-toxic acid and non-toxic base addition salt forms which FTIs, and mTOR inhibitors are able to form. Such compounds which have basic properties can be converted in their pharmaceutically acceptable acid addition salts by treating said base form with an appropriate acid. Appropriate acids comprise, for example, inorganic acids such as hydrohalic acids, e.g. hydrochloric or hydrobromic acid; sulfuric; nitric; phosphoric and the like acids; or organic acids such as, for example, acetic, propanoic, hydroxyacetic, lactic, pyruvic, oxalic, malonic, succinic (i.e. butanedioic acid), maleic, fumaric, malic, tartaric, citric, methanesulfonic, ethanesulfonic, benzenesulfonic, p-toluenesulfonic, cyclamic, salicylic, p-aminosalicylic, pamoic and the like acids.

FTIs and mTOR inhibitors which have acidic properties may be converted in their pharmaceutically acceptable base addition salts by treating said acid form with a suitable organic or inorganic base. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, lysine and the like.

The terms acid or base addition salt also comprise the hydrates and the solvent addition forms that FTIs and mTOR inhibitors are able to form. Examples of such forms are, for instance, hydrates, alcoholates and the like.

Also contemplated for use in methods and compositions described herein are sterochemcially isomeric forms of FTIs and mTOR inhibitors. The term stereochemically isomeric form includes all possible compounds made up of the same atoms bonded by the same sequence of bonds, but having different three-dimensional structures that are not interchangeable. Unless otherwise mentioned or indicated, the chemical designation of a compound encompasses the mixture of all possible stereochemically isomeric forms that the compound may possess. Such mixture may contain all diastereomers and/or enantiomers of the basic molecular structure of the compound. Also contemplated are all stereochemically isomeric forms in pure form or in admixture with each other. Also contemplated are tautomeric forms of FTI and mTOR inhibitor compounds.

Various delivery systems are known and can be used to administer FTIs and mTOR inhibitors as therapeutics. Such systems include, for example, encapsulation in liposomes, microparticles, microcapsules, recombinant cells capable of expressing therapeutic molecule(s) (see, e.g., Wu et al., *J. Biol. Chem.* 262, 4429, 1987), construction of a therapeutic nucleic acid as part of a retroviral or other vector, and the like. Methods of introduction include, but are not limited to, intrathecal, intradermal, intramuscular, intraperitoneal (ip), intravenous (iv), subcutaneous, intranasal, epidural, and oral routes. The therapeutics may be administered by any convenient route, including, for example, infusion or bolus injection, topical, absorption through epithelial or mucocutaneous linings (e.g., oral mucosa, rectal and intestinal mucosa, and the like) ophthalmic, nasal, and transdermal, and may be administered together with other biologically active agents. Pulmonary administration can also be employed (e.g., by an inhaler or nebulizer), for instance using a formulation containing an aerosolizing agent.

In a specific embodiment, it may be desirable to administer the combination pharmaceutical treatments by injection, catheter, suppository, or implant (e g, implants formed from porous, non-porous, or gelatinous materials, including membranes, such as sialastic membranes or fibers), and the like. In another embodiment, therapeutic agents are delivered in a vesicle, in particular liposomes (see, e.g., Langer, *Science* 249, 1527, 1990; Treat et al., in *Liposomes in the Therapy of Infectious Disease and Cancer*, Lopez-Berestein and Fidler (eds.), Liss, N.Y., pp. 353-365, 1989).

In yet another embodiment, any one of the agents used in the combination treatments can be delivered in a controlled release system. In one embodiment, a pump may be used (see, e.g., Langer *Science* 249, 1527, 1990; Sefton *Crit. Rev. Biomed. Eng.* 14, 201, 1987; Buchwald et al., *Surgery* 88, 507, 1980; Saudek et al., *N. Engl. J. Med.* 321, 574, 1989). In another embodiment, polymeric materials can be used (see, e.g., Ranger et al., *Macromol. Sci. Rev. Macromol. Chem.* 23, 61, 1983; Levy et al., *Science* 228, 190, 1985; During et al., *Ann. Neurol.* 25, 351, 1989; Howard et al., *J. Neurosurg.* 71, 105, 1989). Other controlled release systems, such as those discussed in the review by Langer (*Science* 249, 1527 1990), can also be used.

In particular examples a FTI and mTOR inhibitor are administered simultaneously, and by the same mode of administration. In other examples, the pharmaceutical compounds are administered at different times, and either by the same or different more of administration.

The vehicle in which the agent is delivered can include pharmaceutically acceptable compositions of the compounds, using methods well known to those with skill in the art. For instance, in some embodiments, FTIs and mTOR inhibitors typically are contained in a pharmaceutically acceptable carrier. The term "pharmaceutically acceptable" means approved by a regulatory agency of the federal or a state government or listed in the U.S. Pharmacopoeia or other generally recognized pharmacopoeia for use in animals, and, more particularly, in humans. The term "carrier" refers to a diluent, adjuvant, excipient, or vehicle with which the therapeutic is administered. Such pharmaceutical carriers can be sterile liquids, such as water and oils, including those of petroleum, animal, vegetable, or synthetic origin, such as peanut oil, soybean oil, mineral oil, sesame oil, and the like. Water is a preferred carrier when the pharmaceutical composition is administered intravenously. Saline solutions, blood plasma medium, aqueous dextrose, and glycerol solutions can also be employed as liquid carriers, particularly for injectable solutions. The medium may also contain conventional pharmaceutical adjunct materials such as, for example, pharmaceutically acceptable salts to adjust the osmotic pressure, lipid carriers such as cyclodextrins, proteins such as serum albumin, hydrophilic agents such as methyl cellulose, detergents, buffers, preservatives and the like.

Examples of pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, and the like. The therapeutic, if desired, can also contain minor amounts of wetting or emulsifying agents, or pH buffering agents. The therapeutics can take the form of solutions, suspensions, emulsion, tablets, pills, capsules, powders, sustained-release formulations, and the like. The therapeutic can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, and the like. A more complete explanation of parenteral pharmaceutical carriers can be found in Remington: *The Science and Practice of Pharmacy* (19th Edition, 1995) in chapter 95.

Embodiments of other pharmaceutical compositions are prepared with conventional pharmaceutically acceptable counter-ions, as would be known to those of skill in the art.

Therapeutic preparations will contain a therapeutically effective amount of at least one active ingredient, preferably in purified form, together with a suitable amount of carrier so as to provide proper administration to the patient. The formulation should suit the mode of administration.

The combination treatments of this disclosure can be formulated in accordance with routine procedures as pharmaceutical compositions adapted for intravenous administration to human beings. Typically, compositions for intravenous administration are solutions in sterile isotonic aqueous buffer. Where necessary, the compositions may also include a solubilizing agent and a local anesthetic such as lidocaine to ease pain at the site of the injection.

The ingredients in various embodiments are supplied either separately or mixed together in unit dosage form, for example, in solid, semi-solid and liquid dosage forms such as tablets, pills, powders, liquid solutions, or suspensions, or as a dry lyophilized powder or water free concentrate in a hermetically sealed container such as an ampoule or sachette indicating the quantity of active agent. Where one or more of the indicated agents is to be administered by infusion, it can be dispensed with an infusion bottle containing sterile pharmaceutical grade water or saline. Where the FTIs and mTOR inhibitors are administered by injection, an ampoule of sterile water or saline can be provided so that the ingredients may be mixed prior to administration. As indicated above, the combined pharmaceutical agents can be administered together (e.g. including in a single formulation), but can also be administered individually.

The amount of each therapeutic agent that will be effective will depend on the nature of the disorder or condition to be treated, as well as the stage of the disorder or condition. Effective amounts can be determined by standard clinical techniques. The precise dose to be employed in the formulation will also depend on the route of administration, and should be decided according to the judgment of the health care practitioner and each patient's circumstances. Exemplary dosages of the individual compounds are described herein, but myriad other dosage regimens are encompassed by this disclosure. An example of an additional dosage range is 0.1 to 200 mg/kg body weight in single or divided doses. Another example of a dosage range is 1.0 to 100 mg/kg body weight in single or divided doses.

The specific dose level and frequency of dosage for any particular subject may be varied and will depend upon a variety of factors, including the activity of the specific compound, the metabolic stability and length of action of that compound, the age, body weight, general health, sex, diet, mode and time of administration, rate of excretion, drug combination, and severity of the condition of the host undergoing therapy.

The therapeutic compounds and compositions of the present disclosure can be administered at about the same dose throughout a treatment period, in an escalating dose regimen, or in a loading-dose regime (e.g., in which the loading dose is about two to five times the maintenance dose). In some embodiments, the dose is varied during the course of a treatment based on the condition of the subject being treated, the severity of the disease or condition, the apparent response to the therapy, and/or other factors as judged by one of ordinary skill in the art. In some embodiments long-term treatment with the drug is contemplated.

In some embodiments, sustained localized release of the pharmaceutical preparation that comprises a therapeutically effective amount of a therapeutic compound or composition may be beneficial. Slow-release formulations are known to those of ordinary skill in the art. By way of example, polymers such as bis(p-carboxyphenoxy)propane-sebacic-acid or lecithin suspensions may be used to provide sustained localized release.

It is specifically contemplated in some embodiments that delivery is via an injected and/or implanted drug depot, for instance comprising multi-vesicular liposomes such as in DepoFoam (SkyePharma, Inc, San Diego, Calif.) (see, for instance, Chamberlain et al., *Arch. Neuro.* 50:261-264, 1993; Katri et al., *J. Pharm. Sci.* 87:1341-1346, 1998; Ye et al., *J. Control Release* 64:155-166, 2000; and Howell, *Cancer J.* 7:219-227, 2001).

The following examples are provided to illustrate certain particular features and/or embodiments. These examples should not be construed to limit the disclosure to the particular features or embodiments described.

EXAMPLES

Example 1: Three-Agent Combination Therapy for Treatment of HGPS

This example describes a three-drug combination therapy to treat HGPS.

A clinical study can be developed analogous to that described in Gordon et al., *PNAS,* 109:16666/16671, 2012, the contents of which are incorporated by reference in their entirety.

In an exemplary study, children were administered three-drug combinations of lonafarnib at 115 mg/m$^2$ (the FTI component) and pravastatin at 10 mg/oral dose (the statin component), and zoledronic acid. Zoledronic acid was administered intravenously at week one, and months 6, 12, 18, 40-52 and 60 of the treatment trial. At each of time points, treatment consisted of one infusion over a 30 minute period. Initial Infusion: 0.0125 mg/kg body weight, diluted in 0.9% sodium chloride, and infused over 30 minutes. After initial infusion, the recommended dose is 0.1 mg/kg body weight annually. Infusion at 6, 12, and 18 months: 0.05 mg/kg body weight diluted in 0.9% sodium chloride, and infused over 30 minutes. Infusion at 40-52 and 60 months: is 0.1 mg/kg body weight in 50 mL saline. Zoledronic acid may be withheld by the study team if the patient has experienced a recent or poorly healed fracture.

To determine efficacy of the drug combination, children were examined for differences in weight gain; cardiovascular function (e.g. carotid-femoral pulse wave velocity, diagnostic carotid artery ultrasonography, mean distal internal carotid artery velocity, distal common carotid artery far-wall intima media thickness); skeletal function (flexibility and bone density), and auditory (low frequency sensorineural hearing).

Indications of treatment efficacy will include, but are not limited to, weight gain, decrease in carotid-femoral pulse wave velocity (indicating increased arterial flexibility), increased bone flexibility and density, and increased ability to hear at lower range frequencies.

Measurements of bone mass density were made and observed as follows:

This analysis summarizes baseline and one-year BMD data for children with classical progeria. Of 45 children participating in the trial 2, 8 have non-classical forms of the disease and their data were excluded from this summary (case numbers: 21, 27, 33, 34, 35, 38, 43, and 47).

Due to missing measurements, the analyses of total body and hip BMD are based on 32 children; 33 children have data for the comparisons of lumbar spine BMD. [Child #32 is missing all baseline measures; child #42 is missing baseline total body and hip. One-year data are missing for cases #3, 18, and 22.]

Statistical Methods:

The first analysis compares the overall observed percent change in total body, lumbar spine, or hip BMD with zero using the Wilcoxon signed-rank test. In the second analysis, baseline BMD measures or percent change in BMD are compared for the children who continued from Trial 1 (N=21) with the children who were newly enrolled into Trial 2 (N=12). The comparisons between the two groups use the Wilcoxon rank-sum test.

Results:

Table 1 summarizes the overall changes in BMD for the total body, spine, and hip. Median percent increases ranged from 6.1% in the total body to 6.9% in the hip. All percent changes in Table 1 were significantly greater than zero.

Tables 2 through 4 present the BMD comparisons by trial subgroup. The data suggest (Table 2) that total body BMD was higher at baseline in the children continuing from Trial 2 (p=0.06); however, the percent change between baseline and one-year was not statistically significantly different between the two groups (p=0.30). Table 3 compares the two groups with respect to lumbar spine BMD; there were no significant differences between the trial groups at baseline or in percent change. Hip BMD (Table 4) was not different between the trial groups at baseline, nor were the percent changes significantly different.

TABLE 1

Summary of BMD Measures and Percent Change from Baseline

| Site | N | Baseline BMD (g/cm2) Median (range) | One-Year BMD (g/cm2) Median (range) | BMD % Change Median (range) | P-value of % Change† (Wilcoxon signed-rank) |
|---|---|---|---|---|---|
| Total Body | 32 | 0.482 (0.390, 0.643) | 0.507 (0.427, 0.653) | 6.1 (−3.2, 24.7) | <0.0001 |
| Lumbar Spine | 33 | 0.431 (0.349, 0.624) | 0.473 (0.400, 0.674) | 6.8 (−5.6, 30.7) | <0.0001 |
| Hip | 32 | 0.429 (0.369, 0.633) | 0.475 (0.389, 0.625) | 6.9 (−8.8, 35.5) | <0.0001 |

†Comparison of percent change with zero

TABLE 2

Summary of Total BMD and Percent Change by Trial

| | | N | Median | Min | Max | P-value (Wilcoxon rank-sum) |
|---|---|---|---|---|---|---|
| Baseline | Trial 1 | 21 | 0.492 | 0.420 | 0.643 | 0.06 |
| | Trial 2 | 11 | 0.462 | 0.390 | 0.625 | |
| One-Year | Trial 1 | 21 | 0.531 | 0.459 | 0.653 | — |
| | Trial 2 | 11 | 0.491 | 0.427 | 0.605 | |
| Percent Change | Trial 1 | 21 | 7.6 | 1.5 | 14.3 | 0.30 |
| | Trial 2 | 11 | 5.3 | −3.2 | 24.7 | |

TABLE 3

Summary of Lumbar Spine BMD and Percent Change by Trial

| | | N | Median | Min | Max | P-value (Wilcoxon rank-sum) |
|---|---|---|---|---|---|---|
| Baseline | Trial 1 | 21 | 0.435 | 0.369 | 0.606 | 0.61 |
| | Trial 2 | 12 | 0.419 | 0.377 | 0.633 | |
| One-Year | Trial 1 | 21 | 0.485 | 0.398 | 0.609 | — |
| | Trial 2 | 12 | 0.464 | 0.389 | 0.625 | |
| Percent Change | Trial 1 | 21 | 9.1 | −4.1 | 28.4 | 0.10 |
| | Trial 2 | 12 | 5.3 | −8.8 | 35.5 | |

TABLE 4

Summary of Hip BMD and Percent Change by Trial

| | | N | Median | Min | Max | P-value (Wilcoxon rank-sum) |
|---|---|---|---|---|---|---|
| Baseline | Trial 1 | 21 | 0.448 | 0.384 | 0.624 | 0.13 |
| | Trial 2 | 11 | 0.424 | 0.349 | 0.591 | |
| One-Year | Trial 1 | 21 | 0.473 | 0.400 | 0.674 | — |
| | Trial 2 | 11 | 0.459 | 0.404 | 0.567 | |
| Percent Change | Trial 1 | 21 | 6.4 | −3.3 | 14.9 | 0.25 |
| | Trial 2 | 11 | 12.4 | −5.6 | 30.7 | |

Example 2: Survival Analysis of HGPS Patients Treated with a Farnesyltransferase Inhibitor This example shows the benefit to HGPS patient survival from treatment with a farnesyltransferase inhibitor (including treatment in combination with pravastatin and zoledronic acid).

Methods

Survival data of untreated subjects was collected from hospital case studies, newspaper articles, and other publicly available databases. "Untreated subjects" were defined as HGPS-diagnosed subjects who had no exposure to HGPS clinical treatment trial medications. In total, data from 155 subjects; including 100 deceased and 55 living, was used in the analysis, the cut-off date for which was Dec. 3, 2012.

"Treated subjects" were defined as all subjects who were enrolled in one or both of two HGPS farnesyltransferase inhibitor (FTI) clinical treatment trials to date, for any length of time. Treatment conditions for the initial, FTI-only, trial are described in Gordon et al., *PNAS*, 109:16666/16671, 2012. Treatment conditions for the three-drug combination of lonafarnib, pravastatin, and zoledronic acid, are described in Example 1. In total data from 43 subjects; including 4 deceased and 39 living, was included in the analysis.

Kaplan-Meier survival analyses were carried out using SAS statistical analysis software.

Results

One measure of the efficacy of FTI treatment for HGPS is to compare the survival rate of HGPS patients who have received FTI treatment (including treatment in combination with pravastatin and zoledronic acid), with the survival rate of patients who did not receive FTI treatment. This comparison, carried out using standard Kaplan-Meier survival analysis, is shown in FIGS. 1-4. The survival effect of FTI treatment on the entire sample of treated patients vs. untreated patients is presented in FIG. 1, which shows a significant survival benefit due to FTI treatment. To control for possible biases resultant from age, birth-year and other subject characteristics, survival analyses was performed on several subgroups of the subject data, shown in FIGS. 2-4.

Figure 2:
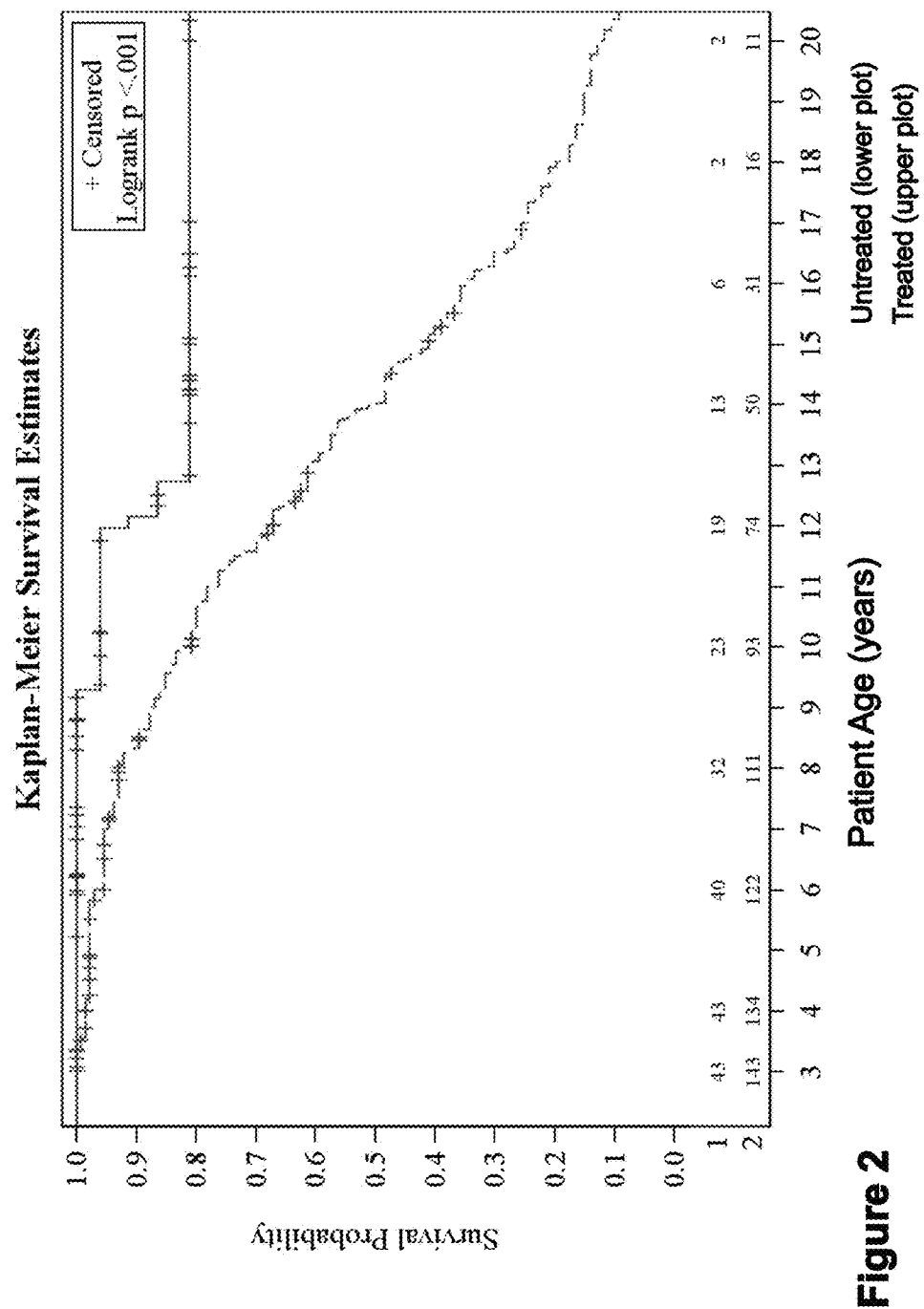
FIG. 2 shows the results of a Kaplan-Meier survival analysis comparing HGPS patients who were with treated with lonafarnib (including patients treated with lonafarnib; pravastatin; zoledronic acid), with patients were not treated with any farnesyltransferase inhibitor. The results shown are restricted to patients starting at three years of age. Untreated subjects are shown in the lower plot. Treated subjects are shown in the upper plot.
Figure 3:
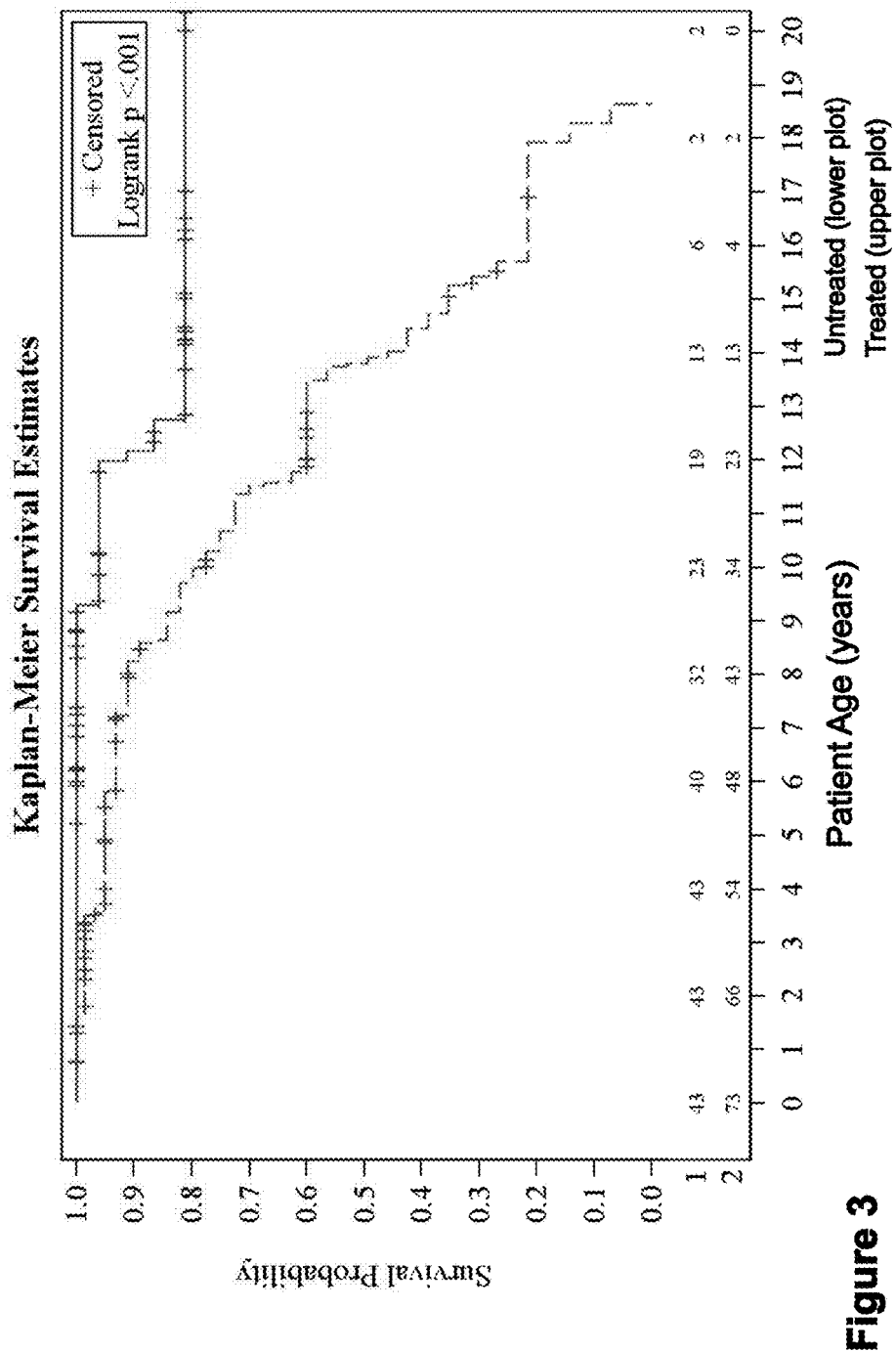
FIG. 3 shows the results of a Kaplan-Meier survival analysis comparing HGPS patients who were with treated with lonafarnib (including patients treated with lonafarnib; pravastatin; zoledronic acid), with patients were not treated with any farnesyltransferase inhibitor. The results shown are restricted to patients born on or after 1991. Untreated subjects are shown in the lower plot. Treated subjects are shown in the upper plot.
Figure 4:
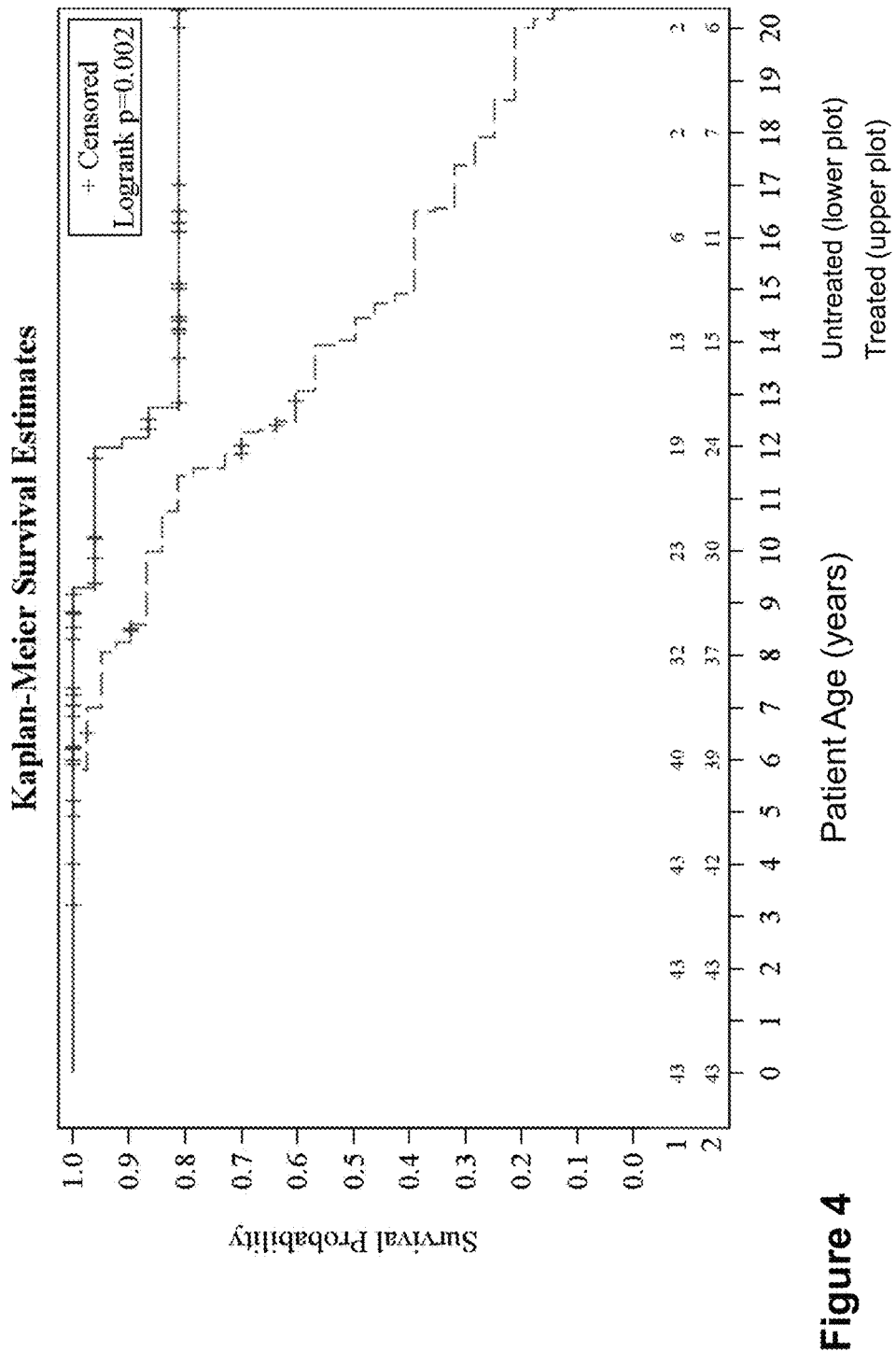
FIG. 4 shows the results of a Kaplan-Meier survival analysis comparing HGPS patients who were with treated with lonafarnib (including patients treated with lonafarnib; pravastatin; zoledronic acid), with patients were not treated with any farnesyltransferase inhibitor. The results shown are restricted to a matched sample of the available data. Untreated subjects are shown in the lower plot. Treated subjects are shown in the upper plot.

FIG. 2 shows the comparison of survival of treated vs. untreated patients, starting at three years of age; FIG. 3 shows the comparison of survival of treated vs. untreated patients, in the subset of patients born on or after 1991; and FIG. 4 shows the comparison of survival of a matched sample of treated vs. untreated patients. In each of FIGS. 2-4, a significant survival effect can be observed in FTI-treated patients, in comparison with untreated patients.

The mean survival age of treated patients vs. untreated patients is shown in FIG. 5. The difference in survival years between the groups is also shown, and demonstrates that regardless of how the subjects were grouped in the survival analyses, a significant increase in mean years of survival can be observed for the FTI treated group. From these analyses it can be concluded that FTI treatment (including treatment in combination with pravastatin and zoledronic acid) if effective at treating HGPS and extending the lives of HGPS patients.

Example 3: Two-Agent Combination Therapy for Treatment of HGPS

This example describes a two drug combination therapy to treat HGPS. A clinical study can be developed as in Example 1, with the difference being that two therapeutic agents are administered instead of three. Children in the study are administered two-drug combinations of lonafarnib (the FTI component) and everolimus (the mTOR inhibitor component). The FTI is administered as described in Example 1.

Everolimus is formulated as tablets for oral administration in 1 mg, 2.5 mg, and 5 mg strengths. Tablets are blister-packed under aluminum foil in units of 10 tablets, which should be opened only at the time of administration as the drug is both hygroscopic and light-sensitive. Dosing can be initiated at 3 mg/m$^2$/day for a period of 4 months. This is lower than the body-size adjusted optimum biologic dose (10 mg/day) established in previous adult phase I and II studies of in cancer patients, which would be equivalent to 5 mg/m$^2$. If tolerance of 3 mg/m$^2$ is established, patients will be dose escalated to 5 mg/m$^2$ for a period of two years. Pharmacokinetics will be performed at month 4 for 3 mg/m$^2$ dose, and at one year for 5 mg/m$^2$ dose. Doses will be adjusted according to the toxicities. The body surface area (BSA) will be calculated based on an accurate height and weight measurement performed according to institutional guidelines. Each patient's dose will be rounded to the nearest tablet size for those who can swallow pills. At follow-up evaluations, everolimus doses will be adjusted for changes in body surface area.

The Clinical outcomes can be determined as described in Example 1 and detailed in Gordon et al.

Example 4: Combination Therapies for Treatment of Atherosclerosis

This example describes use of the two-drug combination therapies described herein to treat atherosclerosis.

Olive et al. (*Arterioscler. Thromb. Vasc. Biol.,* 30:2301-2309, 2010) describe the correlation between progerin and cardiovascular disease, atherosclerosis in particular. The two drug combination therapies described in Example 3 can be tested to treat atherosclerosis.

Patients having atherosclerotic vascular thickening and associated high blood pressure can be administered either the three-drug combination, four-drug combination, or a control over the course of a one-year study. Patients can be monitored every three months for changes in disease indicators. Exemplary indicators of improvement in response to the three or four drug therapies include the decreases of arterial thickness and increased vascular flexibility as described in Example 1 and detailed in Gordon et al.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A method for treating Hutchinson-Gilford Progeria Syndrome, comprising:
    administering to a patient in need of such treatment a therapeutically effective amount of two active ingredients consisting essentially of:
    a farnesyltransferase inhibitor (FTI); and
    an mTOR inhibitor
wherein the two active ingredients are administered simultaneously or are not administered simultaneously.

2. The method of claim 1, wherein the FTI is lonafarnib.

3. The method of claim 1, wherein the mTOR inhibitor is everolimus.

4. The method of claim 2, wherein the lonafarnib is administered at a dosage between 115 mg/m$^2$ and 150 mg/m$^2$.

5. The method of claim 1, wherein the two active ingredients are administered simultaneously.

6. The method of claim 1, wherein the two active ingredients are not administered simultaneously.

* * * * *